(12) United States Patent
Sawafta

(10) Patent No.: US 6,539,334 B1
(45) Date of Patent: Mar. 25, 2003

(54) AUTOMATED WEIGHING STATION

(75) Inventor: Reyad I. Sawafta, Greensboro, NC (US)

(73) Assignee: TransTech Pharma, Inc., High Point, NC (US)

( * ) Notice: Subject to any disclaimer, the term of this patent is extended or adjusted under 35 U.S.C. 154(b) by 120 days.

(21) Appl. No.: 09/611,393

(22) Filed: Jul. 7, 2000

(51) Int. Cl.[7] .............................................. G01G 19/03
(52) U.S. Cl. .................... 702/175; 702/173; 177/25.11; 141/165
(58) Field of Search ........................ 702/173; 177/25.11, 177/25.12, 25.13, 26, 1, 2, 3, 5, 6, 35, 161; 700/305; 705/414; 414/416.09; 141/83, 165

(56) References Cited

U.S. PATENT DOCUMENTS

| | | | |
|---|---|---|---|
| 4,913,198 A | * | 4/1990 | Hayahara et al. ............ 141/103 |
| 5,660,792 A | | 8/1997 | Koike |
| 5,769,775 A | | 6/1998 | Quinlan et al. |

FOREIGN PATENT DOCUMENTS

| | | | |
|---|---|---|---|
| DE | 19722091 A1 | * 12/1998 | ............ G01G/11/00 |
| EP | 1003020 A1 | 5/2000 | |
| EP | 0769686 B1 | 12/2001 | |

OTHER PUBLICATIONS

Brochure—"Balance Automator™, Round–the–Clock Weighing Station," LIT–BO2–1098, Bohdan Automation, Inc. (1998).

Brochure—"Automation Your Way Today, Automated Weighing/Labeling Workstation," dlit01 199, Bohdan Automation, inc. (date unknown).

Brochure—"Automated Weighing, Automated Labeling, Synthesis Support, High Throughput Synthesis, Process Development," LIT–GEN1–100, Bohdan Automation, inc. (date unknown).

Brochure—J–KEM Scientific Custom Robotics & Accessories; www.jkem.com.

International Search Report mailed Nov. 13, 2001 corresponding to PCT/US 01/41301.

* cited by examiner

*Primary Examiner*—John Barlow
*Assistant Examiner*—Anthony T. Dougherty
(74) *Attorney, Agent, or Firm*—Charles W. Calkins; Cynthia B. Rothschild; Kilpatrick Stockton LLP

(57) ABSTRACT

An automated weighing station is provided which is advantageous for automatically weighing samples generally disposed in containers in an array of racks. The weighing station comprises a sample handling assembly which is operably connected to a balance, allowing a moveable sample carrier to bring samples into position beneath the balance and sample handling assembly, thereby minimizing the movement of individual samples in order to accomplish weighing. A weighing system that provides flexibility and convenience in generating and transforming a variety of data sets associated with measurements accomplished using the weighing apparatus is also provided.

69 Claims, 11 Drawing Sheets

AUTOMATED WEIGHING STATION

FIELD OF THE INVENTION

The present invention relates to a weighing apparatus. An embodiment of the present invention is advantageous for automatically weighing small samples generally disposed in containers in an array of racks. The invention also relates to weighing systems that provide flexibility and convenience in generating and transforming a variety of data sets associated with measurements accomplished using the weighing apparatus.

BACKGROUND

Recently, the proliferation of combinatorial libraries in high throughput synthesis and screening (HTS) programs have led to an ever increasing emphasis on automation. The ability to prepare and test a large number of compounds quickly can provide a competitive advantage. Thus, automated preparation and evaluation has become a key process in lead discovery.

The recent explosion in the number of compounds available for screening, and the expected increase in compounds with the development of automated chemical synthesis, has meant that a large number of pharmaceutical and other chemical companies are in need of automated weighing of such compounds. However, several difficulties have been encountered in attempts to provide a fast, efficient, and cost-effective solution to the problem of automatically weighing large numbers of small samples.

Proposed solutions which simply implement robotic methods to remove and replace samples from racks to facilitate weighing present significant problems. Robotic fingers have difficulty in grasping individual samples for removal from among an array of closely placed samples in a rack. Certain devices function only with flat bottom containers, which are more difficult to return to the rack after weighing. Misplacement during return may result in spilling of the sample contents, or breakage of one or more samples (possible leading to contamination of on e or more samples).

A major difficulty unsolved by current devices is the lack of speed when weighing a large number of samples. Current devices generally employ a robotic sample transfer assembly, which retrieves a sample from an array, transfers the sample to a separate balance, and then returns the sample container to a particular position in a holder, such as a test tube rack. Although some such systems may have the ability to identify the particular sample, and associate the sample with the measurement taken to enable later data recordation and processing, systems currently employed require a large amount of inefficient and time-consuming movement. The sample must be plucked from an array, moved to the balance, retrieved from the balance, moved back into position relative to the array, and returned to the sample's original position. Thus, having the balance a considerable distance from the actual sample position within an array leads to a great deal lost time in moving each sample to and from the balance.

Current devices also handle a relatively limited number of samples during each run. It would be advantageous to provide an automated system which is capable of handling a larger number of samples than those devices currently available.

Accordingly, it is one object of the present invention to provide an automated weighing system which handles a larger number of samples per run than currently available devices. It is also an objection of the invention to accomplish weighing of a large number of samples in less time, and with increased handling efficiency and reliability. Additionally, another object of the invention is to provide a weighing system allowing increased control of an automated weighing apparatus, and increased versatility in data collection, storage and transformation.

SUMMARY OF THE INVENTION

The present invention provides a solution to many current problems associated with automated weighing of large numbers of samples. One advantage is that the overall movement of individual samples to accomplish the weight measurement is minimized. This reduces the time required, and reduces the likelihood of malfunctions such as breakage of sample containers and/or contamination of samples.

Accordingly, in one aspect the invention relates to an automated weighing station comprising a support frame, a balance secured to the support frame, a sample handling assembly operably connected to the balance and secured to the balance, a moveable carrier for moving samples into position beneath the sample handling assembly, a lift assembly positioned beneath the moveable carrier and the sample handling assembly for lifting samples into position to be accessed by the sample handling assembly, and a control system for controlling the sample handling assembly, the lift assembly, and the moveable carrier in a coordinated manner, and for storing weight measurements of individual samples. The control system also provide a user interface.

In another aspect, the invention relates to a method of weighing multiple individual samples comprising moving an ordered array of sample containers beneath a stationary sample handling assembly, elevating at least one sample container, reversibly securing the at least one sample container to a gripper assembly of the stationary sample handling assembly, and returning the at least one sample container to the ordered array after a weight measurement is taken, wherein the gripper assembly is connected to a balance, and is disengaged from other components of the sample handling assembly while the weight measurement is taken.

In yet another aspect, the invention relates to a weighing system for automated weighing of samples comprising a support frame; a balance secured to the support frame; a sample handling assembly operatively connected to the balance and secured to the balance; a moveable carrier for moving samples into position beneath the sample handling assembly; a lift assembly positioned beneath the moveable carrier and the sample handling assembly for lifting samples into position to be accessed by the sample handling assembly; and a data handling system for storing and processing of weight measurements of the samples.

The invention provides many of the benefits described herein by virtue of the close association of the sample handling assembly, including the gripper assembly, with the balance where the weight measurement is taken. The benefits provided by the invention are described in greater detail below.

BRIEF DESCRIPTION OF THE DRAWINGS

FIG. 10 is a top elevational view of the sample lift assembly.

In the Figures, like reference characters indicate corresponding parts.

DETAILED DESCRIPTION OF THE INVENTION

Figure 1:
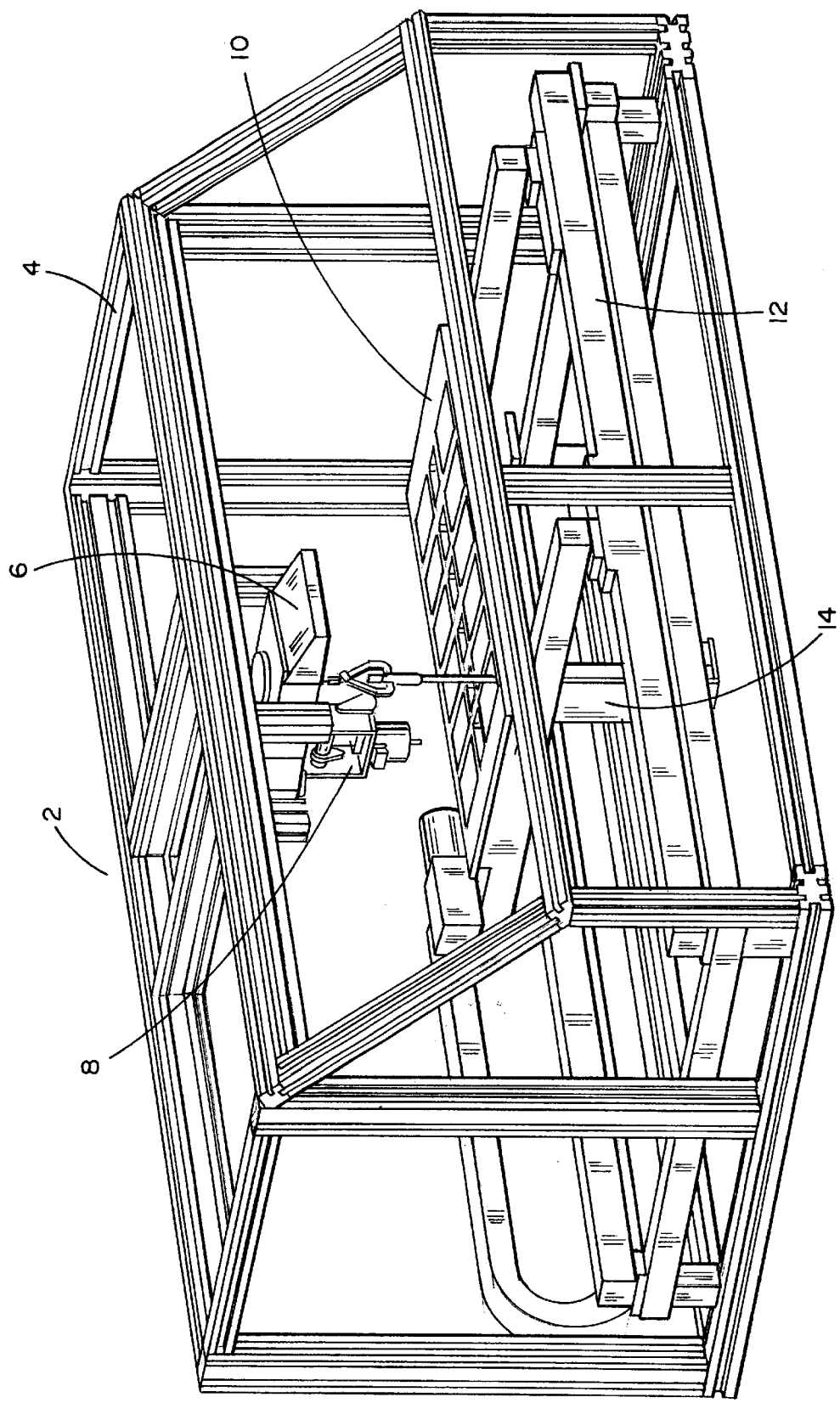
FIG. 1 is a front perspective view of one embodiment of the apparatus of the invention.

The present invention provides solutions to many problems associated with automated weighing of multiple samples. In particular, the present invention allows large numbers of samples to be weighed rapidly. The invention also allows samples to be weighed with decreased opportunity for breakage and/or sample contamination.

Accordingly, in one aspect the invention relates to an automated weighing station comprising a support frame, a balance secured to the support frame, a sample handling assembly operably connected to the balance and secured to the balance, a moveable carrier for moving samples into position beneath the sample handling assembly, a lift assembly positioned beneath the moveable carrier and the sample handling assembly for lifting samples into position to be accessed by the sample handling assembly, and a control system for controlling the sample handling assembly, the lift assembly, and the moveable carrier in a coordinated manner, and for storing weight measurements of individual samples. The moveable carrier is coordinated with the operation of the lift assembly and the sample handling assembly via multiple positioning sensors which output to the control system, allowing rapid and safe handling of the samples, as well as providing data allowing each sample to be individually identified with its corresponding weight measurement when the data is stored or transferred in electronic form.

In a preferred embodiment, the sample handling assembly further comprises a gripper assembly comprising arms, one end of each arm being pivotably connected along a common pivot axis, and the opposite end of each arm comprising a gripper finger adapted to directly contact a sample container; a spring tensioner urging the arms toward one another; and a powered mechanical drive component in communication with the gripper assembly. More preferably, the mechanical drive component operates intermittently to spread the gripper arms against the force of the spring tensioner, thereby increasing the distance between the gripper fingers of the respective gripper arms such that a sample may be received therein, to be gripped by the fingers when the mechanical drive component releases the arms to return to a closed position as urged by the spring tensioner. The gripper assembly is designed to be small and light enough such that the net weight of individual samples is accurately weighed and recorded while the gripper assembly is operable connected to a component of the balance to actuate the weighing mechanism of the balance. When the actual weight measurement is accomplished, the mechanical drive component is dissociated from the gripper assembly, such that it does not interfere with an accurate measurement.

In another preferred embodiment, the moveable carrier comprises a sample rack carrier and a carrier support unit. More preferably, position sensors are provided which are adapted to communicate the position of the sample rack carrier in relation to the gripper assembly to the control system such that weight measurements of individual samples are stored electronically, and are associated with an individual sample by at least one identifying characteristic. Also more preferably, the sample racks are characterized by an asymmetric shape which requires that the sample racks be placed in the sample rack carrier in only one possible orientation relative to the moveable carrier. Also more preferably, a scanner is provided for determining the identity of sample racks within an array of racks held by the sample rack carrier. Also more preferably, the sample rack carrier comprises openings such that the scanner may determine the identity of sample racks disposed within the interior of the array of racks. More preferably, the sample racks are identified by the scanner utilizing a bar coding system. The sample rack carrier may be adapted to hold at least one rack which is adapted to hold a plurality of sample containers. More preferably, the sample rack carrier is adapted to allow access by the lift assemble to at least one sample container from beneath the sample rack carrier. This feature of the present invention provides significant benefits by allowing the overall movement of individual samples to be minimized, and controlled, because samples are moved in a short, substantially vertical path from the sample rack to the gripper assembly.

In a preferred embodiment, the carrier support unit further comprises at least one powered mechanical drive component adapted to provide controlled forward and rearward, left and right movement of the sample rack carrier. More preferably, the at least one powered mechanical drive component comprises a first electric motor controlling forward and rearward movement, and a second electric motor controlling left and right movement of the sample rack carrier. Additionally, position sensors outputting to the control system provide data allowing the individual identity of sample to be associated with their respective weight measurements as stored data.

In another preferred embodiment, the lift assembly comprises a housing; a powered mechanical drive component connected to the housing; and a lift shaft operably connected to the powered mechanical drive component, wherein the powered mechanical drive component provides controlled upward and downward movement of the lift shaft. More preferably, the lift shaft further comprises a tip which is adapted to receive the bottom portion of a sample container. More preferably, the tip is adapted to receive a bottom portion of a sample container, the shape of which is selected from the group consisting of rounded, conical, flat-ended cubical, and flat-ended circular. Most preferably, the powered mechanical drive component comprises an electric motor having a pulley engaged to a belt member, the distal portion of which engages a second pulley, and wherein the belt member is attached to a lift shaft mount to provide upward and downward motion of the lift shaft which is connected to the lift shaft mount. Position sensors allow coordination of the lift shaft movement with sample position relative to the moveable carrier and the sample handling assembly. These position sensors output to the control system to facilitate rapid but safe and efficient sample handling in conjunction with the operation of the sample handing assembly.

In another preferred embodiment, the automated weighing station further comprises a housing adapted to isolate a gripper assembly of the sample handling assembly. More preferably, the housing comprises a first sensor associated with an aperture for receiving a sample through a bottom plate of the housing, and a second sensor positioned adjacent to the gripper assembly, the first and second sensors allowing determination of a lowered position and a lifted position, respectively, of the sample. Most preferably, the housing further comprises at least one aperture for the introduction of gases for atmospheric control within the housing. The sensors output to the control system, allowing control of other moving components of the station, in conjunction with sample movement into, and out of, the housing.

In another aspect, the invention relates to a method of weighing multiple individual samples comprising moving an ordered array of sample containers beneath a stationary sample handling assembly, elevating at least one sample container, reversibly securing the at least one sample container to a gripper assembly of the stationary sample handling assembly, and returning the at least one sample container to the ordered array after a weight measurement is taken, wherein the gripper assembly is connected to a balance and is disengaged from other components of the sample handling assembly while the weight measurement is taken.

In a preferred embodiment, the weight of a sample within the individual sample container is between about 0.01 mg and about 500 g. More preferably, the weight of a sample within the individual sample container is between about 0.1 mg and about 50 g. Most preferably, the weight of a sample within the individual sample container is between about 1 mg and about 5 g.

In a preferred embodiment, the weight of a sample within the individual sample container is between about 1 mg and about 100 mg. More preferably, the weight of a sample within the individual sample container is between about 2 mg and about 50 mg. Most preferably, the weight of a sample within the individual sample container is between about 5 mg and about 25 mg.

The design of the gripper assembly and its operation by the mechanical drive component of the sample handling assembly allows accurate and precise measurements of net sample weight.

In yet another aspect, the invention relates to a weighing system for automated weighing of samples comprising a support frame; a balance secured to the support frame; a sample handling assembly operatively connected to the balance and secured to the balance; a moveable carrier for moving samples into position beneath the sample handling assembly; a lift assembly positioned beneath the moveable carrier and the sample handling assembly for lifting samples into position to be accessed by the sample handling assembly; and a data handling system for storing and processing of weight measurements of the samples.

In a preferred embodiment, the data handling system comprises a balance; computer software; and computer hardware; wherein the data handling system is adapted to communicate weight measurements to computer software and hardware. More preferably, the data handling system further comprises one or more data collectors positioned and adapted to transmit information to a computer control unit, thereby allowing coordinated movement of samples via the sample handing assembly, the moveable carrier, and the lift assembly, wherein the information is coordinated by the computer control unit with the storage of weight measurement transmitted by the balance for individual samples. Most preferably, the data handling system further comprises a scanner for detection of the position and identity of sample racks on the moveable carrier; at least one position sensor associated with the moveable carrier; and at least one sample position sensor associated with the sample handling assembly.

In another preferred embodiment, the computer hardware of the data handling system comprises one or more of the following: a display; data entry apparatus; a processor; an interface to the weighing apparatus; a printer or other output apparatus; electronic interfaces among the component parts; and memory.

In another preferred embodiment, the computer software of the data handling system comprises an operating system; a database program; a report generating program; a data-receiving program for receiving data from the weighing apparatus; and a control program for controlling the weighing apparatus. More preferably, the report generating program is adapted to provide data comprising individual sample identification related one or more of sample rack identity, sample position, tare weight of a sample container, gross weight of sample and sample container, and net weight of sample. More preferably, the data is originally stored in a format selected from the group consisting of ASCII text, binary, and ODBC (object database connectivity format). Most preferably, the data is originally stored in ASCII text format. Other formats may also be employed for data storage and transfer in particular situations.

Referring now to the Figures, it should be noted that like part numbers carry over from figure to figure, and describe the same part in all figures. Referring in particular to FIG. 1, a front perspective view of one embodiment of the automated weighing station 2 of the invention is shown. Enclosure and support frame 4 is shown supporting balance 6 and sample handling assembly 8. Also shown is sample lift assembly 14, sample rack carrier 10, and carrier support unit 12.

Frame 4 also provides support for materials which may be used in conjunction with frame 4 to enclose the automated weighing station 2. Frame 4 may be constructed so as to allow access via a front, lift-type door in a conventional fashion, and/or via side access door openings, such that samples may be easily accessed before, during, or at the conclusion of an automated weighing run.

Sample lift assembly 14 functions to raise an individual sample to facilitate access to the sample by the sample handling assembly 8. Accordingly, sample racks in sample rack carrier 10 have apertures beneath each individual sample compartment to allow access from below the sample. Carrier support unit 12 stably supports sample rack carrier 10, and transports carrier 10 laterally to allow each individual sample to be brought into handling positions beneath sample handling assembly 8.

Figure 2:
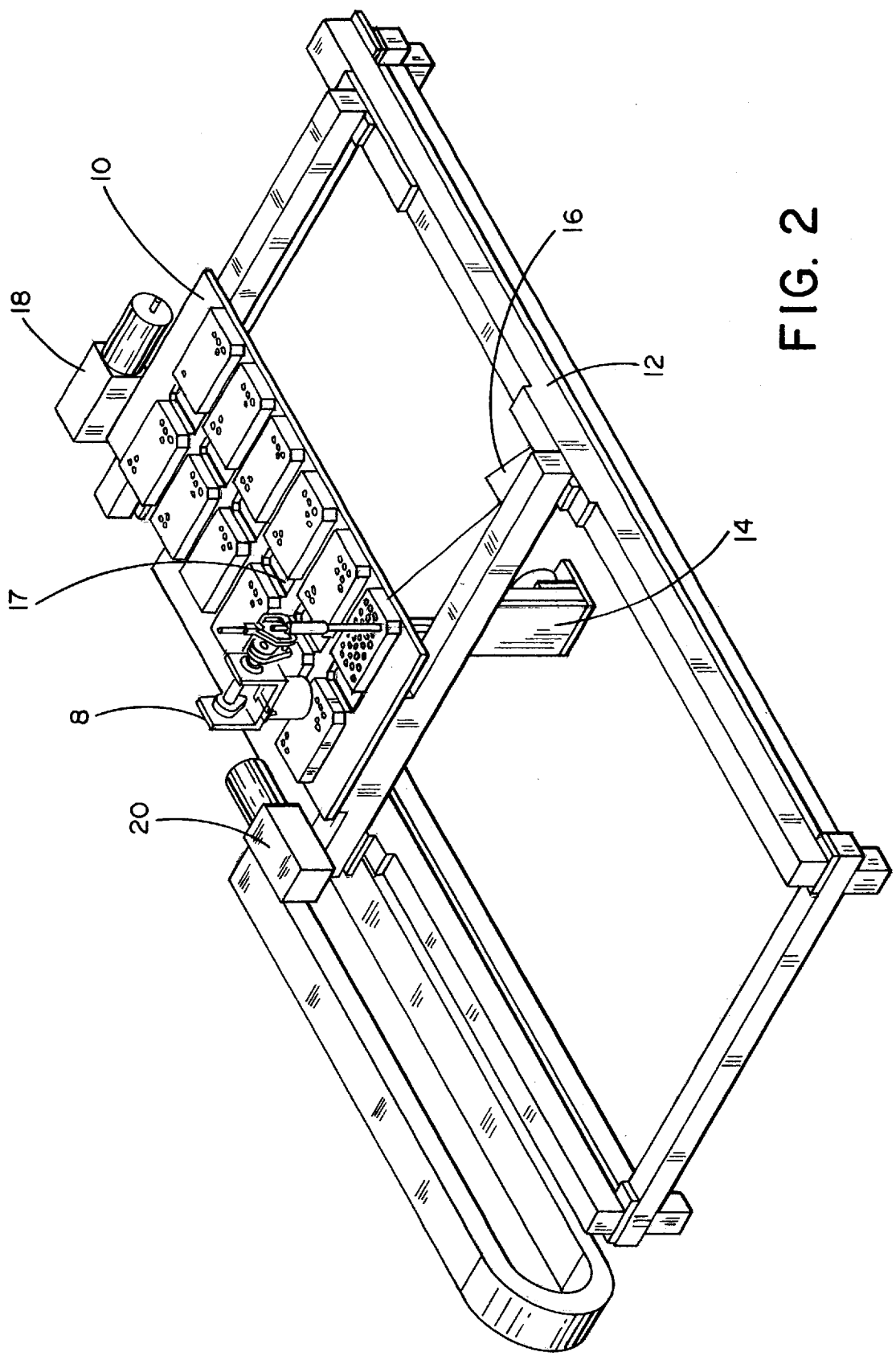
FIG. 2 is a cut-away, top perspective view of the apparatus of the invention (balance and upper frame portion not shown).
Figure 3:
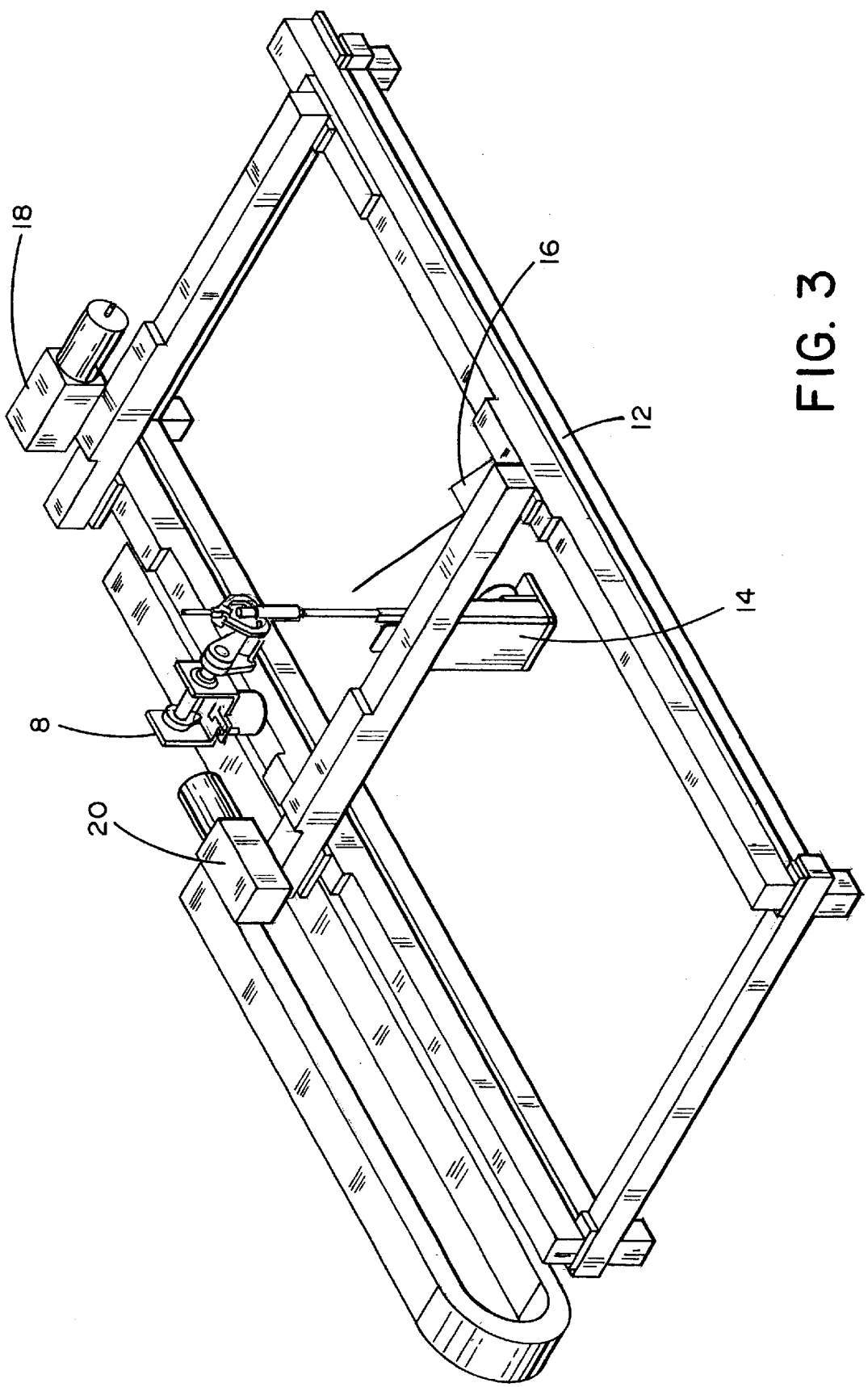
FIG. 3 is a cut-away, top perspective view of the apparatus of the invention as in FIG. 2 (sample racks and carrier not shown).

FIG. 2 shows an embodiment of the apparatus of the invention, without showing frame 4 or balance 6 as shown in FIG. 1. Motors 18 and 20 provide power for left-right, front-back movement of sample rack carrier 10 on carrier support unit 12. Scanner 16 reads identifying information on the end of each sample rack, e.g. a bar code. In FIG. 2, scanner 16 is shown reading the front row of racks in carrier 10. When the rear row of racks is being analyzed, scanner 16 reads the identifying information through apertures 17 in carrier 10. Because of asymmetry in rack design, samples positioned within each rack are necessarily identified by rack identification. FIG. 3 is very similar to FIG. 2, except the sample racks and sample rack carrier 10 are not shown. Sample lift assembly 14 is shown mounted on carrier support unit 12, and interacting with a sample container to facilitate reception of a sample by sample handling assembly 8.

Figure 4:
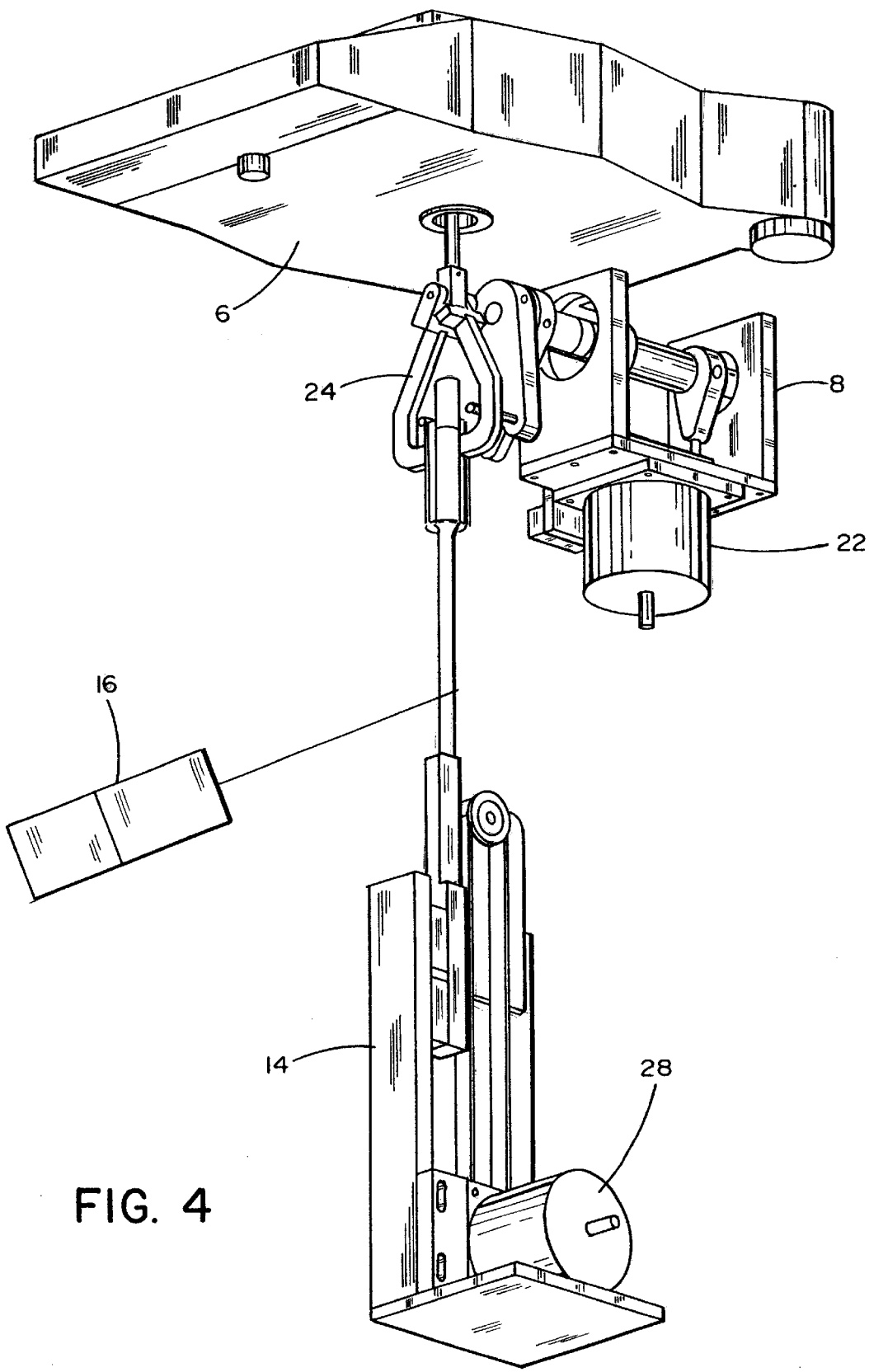
FIG. 4 is a perspective view of the balance, sample handling, sample lift, and rack detection/identification components of the apparatus (viewed as from lower right to upper left of the view of FIG. 1 -sample racks, carrier, and frame not shown).

FIG. 4 shows the relative positioning and interaction between balance 6, sample handling assembly 8, and sample lift assembly 14. Gripper assembly 24 is shown holding a sample for weighing in conjunction with sample lifting assembly 14, powered by lifting motor 28. Sample handling assembly 8 includes gripper spreader motor 22. Although sample racks and sample rack carrier 10 are not shown in FIG. 4, scanner 16 is shown for the purpose of illustrating the relative positioning of components.

Figure 5:
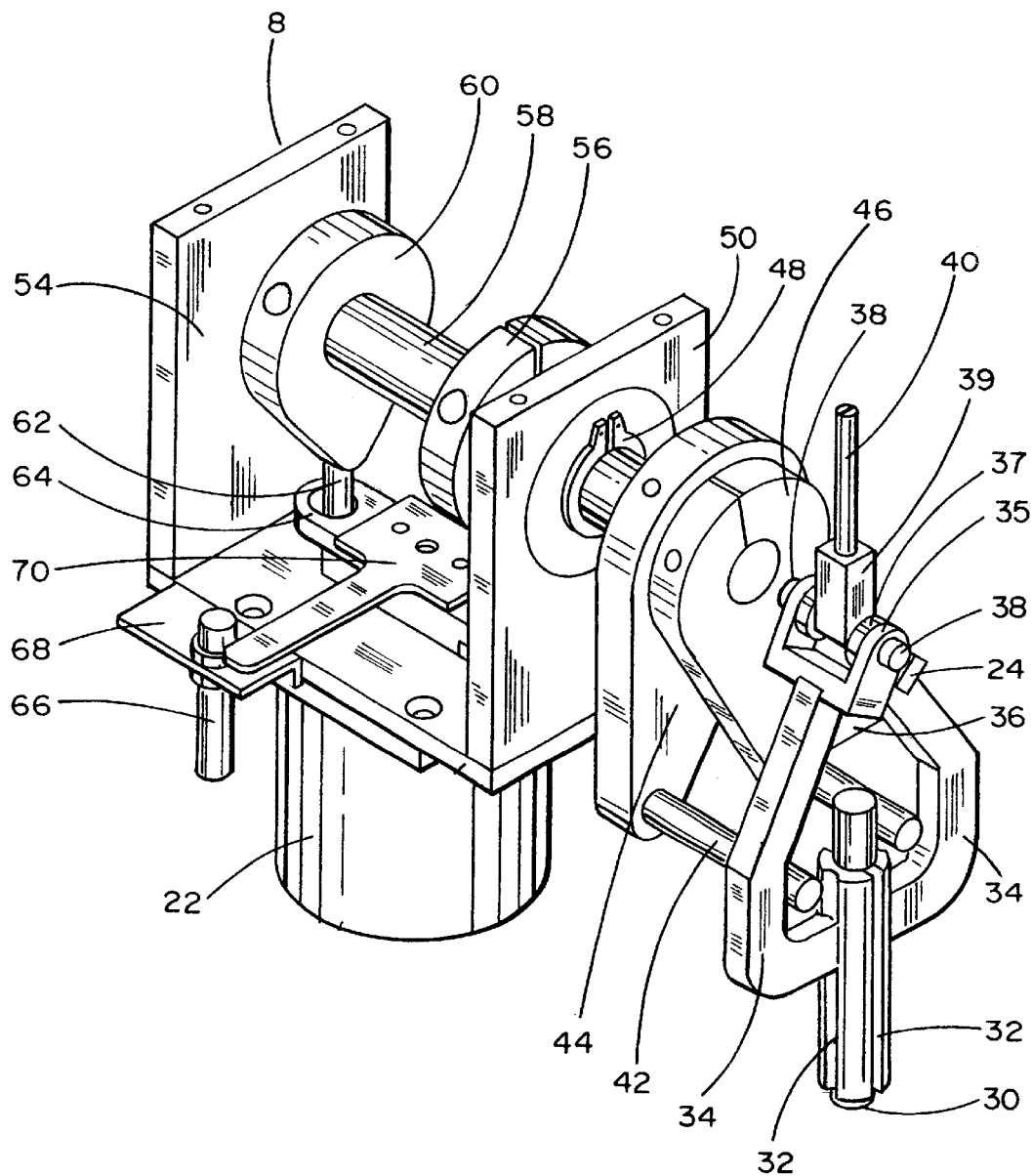
FIG. 5 is a top perspective view of the sample handling assembly.
Figure 6:
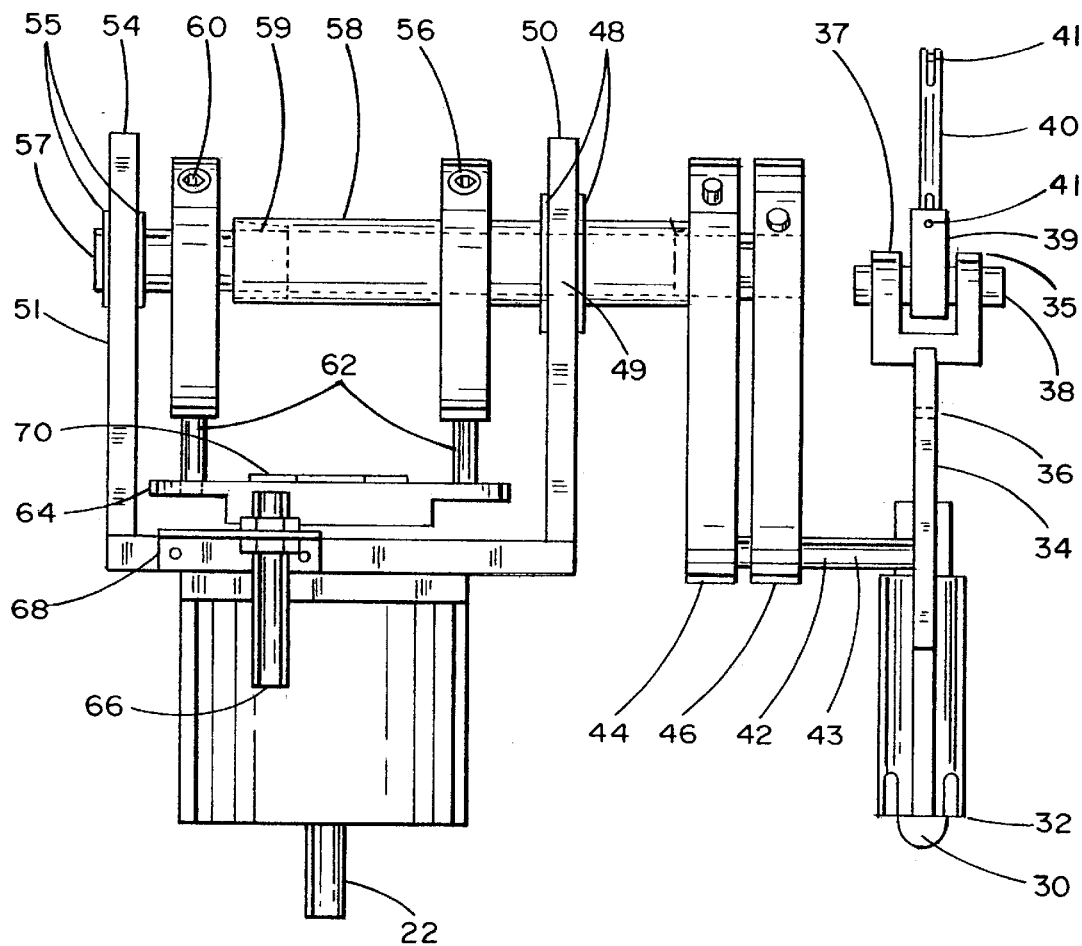
FIG. 6 is a side elevational view of the sample handling assembly.

FIG. 5 is an enlarged depiction of sample handling assembly 8. Gripper assembly 24 comprises gripper fingers 32 which directly contact sample container 30. Gripper fingers 32 are connected to gripper arms 34 which are urged toward one another by spring 36. Outer clevis 35 and inner clevis 37 connect the gripper arms 34 to mounting block 39 via shoulder screws 38. Mounting block 39 is connected to balance shaft 40 via dowel pin 41 (as shown in FIG. 6). Balance shaft 40 is connected to balance 6 (see FIG. 4) via dowel pin 41 (see FIG. 6).

Gripper arms 34 of gripper assembly 24 are spread (against the tension provided by spring 36) by dowels 42 and 43, which are connected to arm spreaders 44 and 46, respectively. Arm spreader 44 is connected to and actuated by outer shaft 58. Arm spreader 46 is connected to and actuated by inner shaft 57. Outer shaft 58 and inner shaft 57 are supported by bearing 49 as they pass through front mount 50. This connection is secured by snap rings 48, which are disposed forward and rearward of front mount 50. The rearward end of outer shaft 58 terminates prior to rear mount 54, and is supported in relation to inner shaft 57 by bronze bushing 59. Inner shaft 57 continues rearward through rear mount 54, where it is supported by bearing 51, and secured by snap rings 55.

Outer arm rotator 56 and inner arm rotator 60 are connected to outer shaft 58 and inner arm shaft 57, respectively. Arm rotators 56 and 60 are connected to rotator 64 via. dowels 62. Rotator 64 is powered by stepper motor 22, to actuated arm rotators 56 and 60. The operation of rotator 64 is controlled by sensor 66 (e.g. an omron sensor), which operators via sensor flag 70. Sensor bracket 68 provides the platform for mounting of sensor 66 and sensor flag 70. The sensor assembly allows the coordination of the operation of sample handling assembly 8 with other components of the apparatus. In particular, operation of sample handling assembly 8 is coordinated with the operation of sample lift assembly 14.

Figure 7:
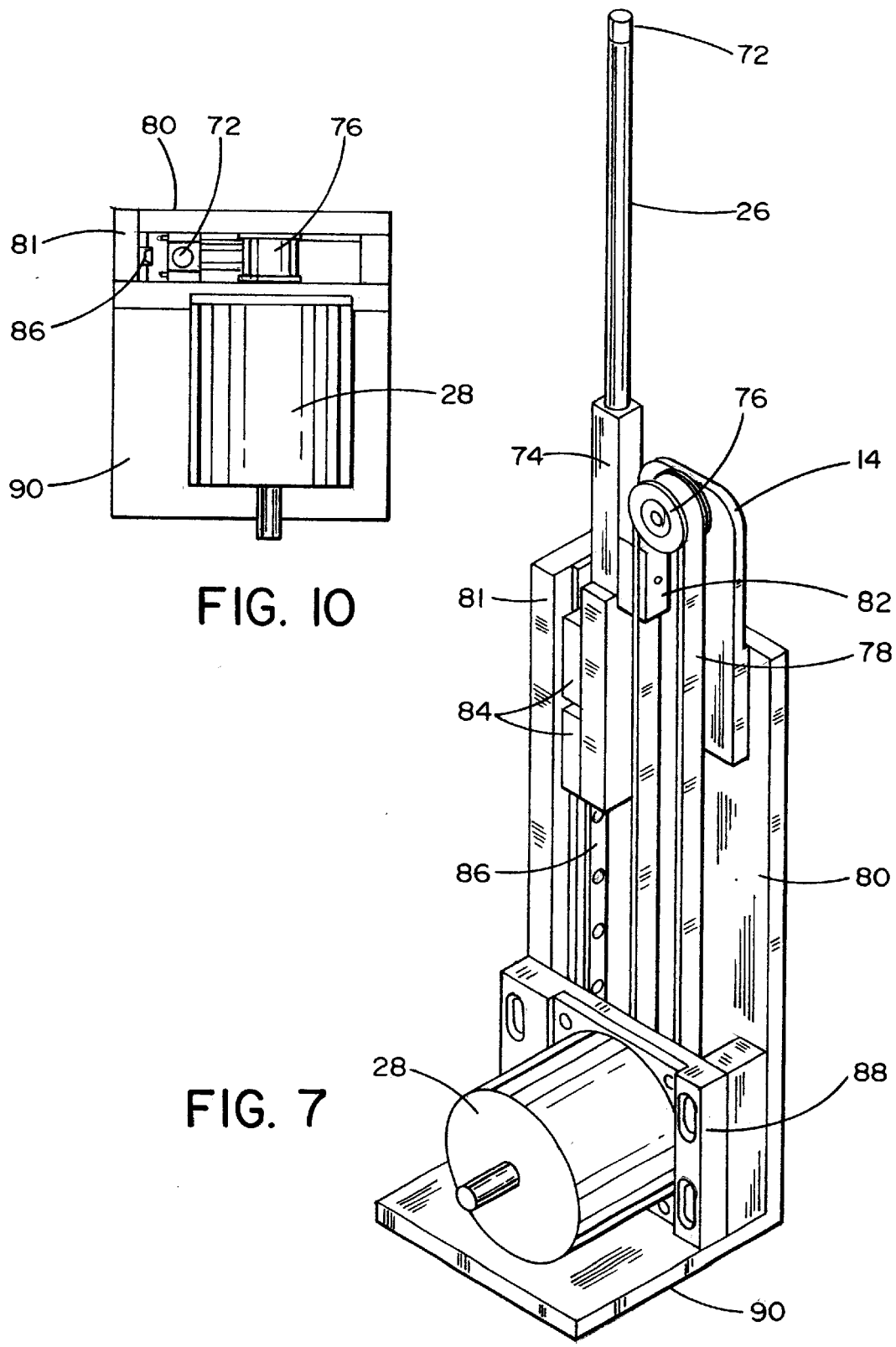
FIG. 7 is a perspective view of the sample lift assembly (viewed as from the upper right rear to the lower, left front of the view of FIG. 2).
Figure 8:
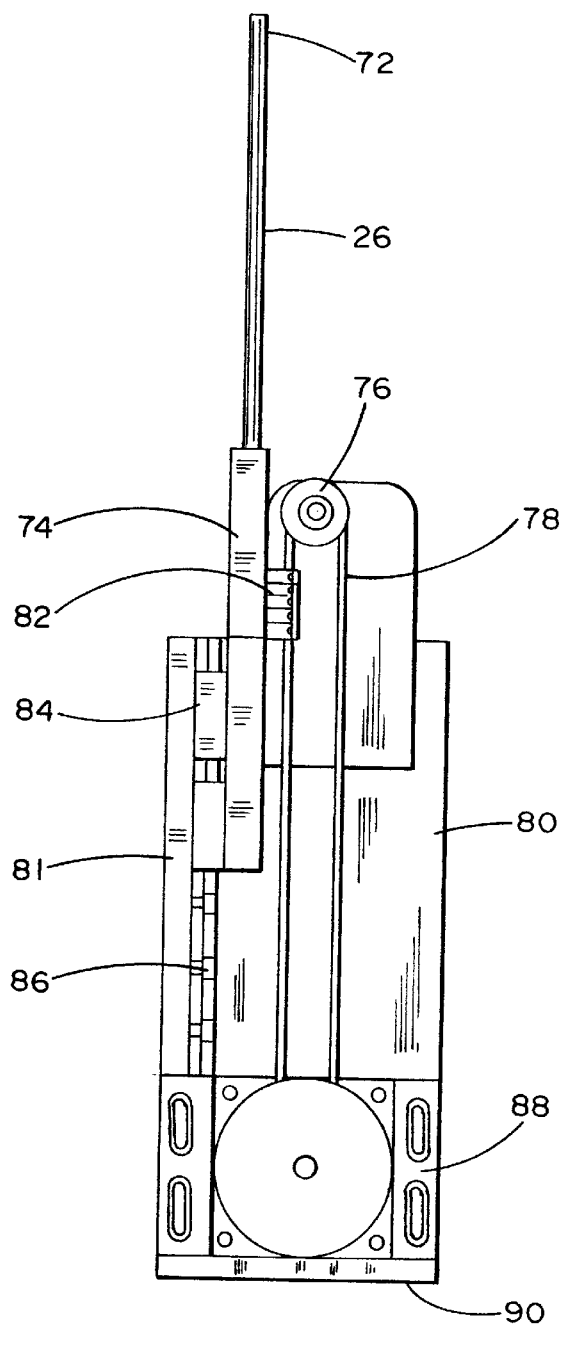
FIG. 8 is an elevational view of the sample lift assembly (viewed as from the right of FIG. 2).
Figure 9:
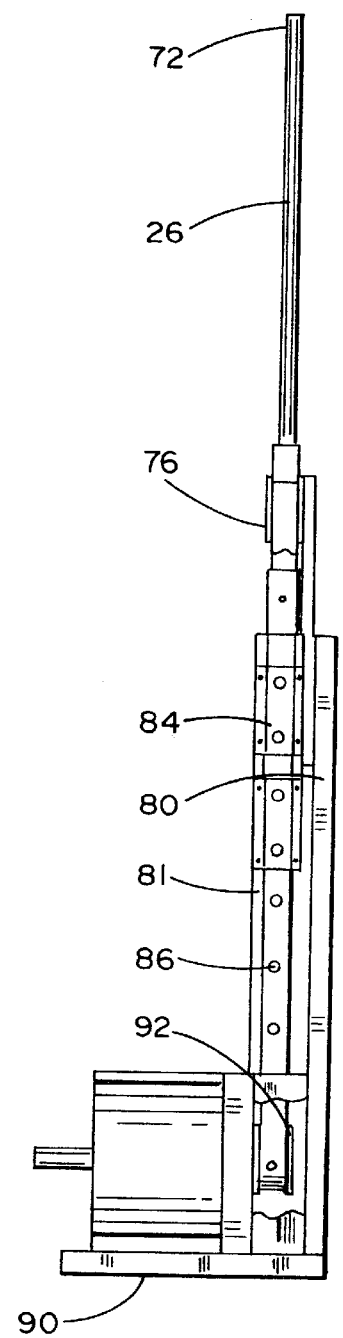
FIG. 9 is an elevational view of the sample lift assembly (viewed as from the right of FIG. 8).

FIGS. 7–10 show various detailed views of sample lift assembly 14. FIG. 7 is a front perspective view of the assembly; FIG. 8 is a front elevational view; FIG. 9 is a side elevational view (as from the right of FIG. 8); and FIG. 10 is a top elevational view of the assembly.

Lift motor 28, mounted in bracket 88 on platform 90, powers drive belt 78 via pulley 92. At the upper end of sample lift assembly 14, pulley 76 is mounted on an extension of rear mount 80 to carry drive belt 78. Side mount 81 is connected along one edge to rear mount 80, at its bottom to platform 90, and on the lower portion of its front side to bracket 88. On the side of drive belt 78 proximal to side mount 81, bracket 82 is connected to lift shaft mount 74. On the opposite side of lift shaft mount 74, brackets 84 provide a mounting platform for sensor components and travel stops, which are coordinated with sensor components and travel stops 86 mounted on side mount 81 to control range of operation and range of travel of lift shaft mount 74 in conjunction with the operation of lift motor 28 and the drive assembly. Lift shaft 26 is mounted in lift shaft mount 74 and terminated at the upper end with tip 72. Tip 72 may be configured variously, depending on the shape of the bottom of sample container 30. In a preferred embodiment, tip 72 is cup shaped at the top to allow handling of containers with round bottoms. Conical or flat bottom containers may be handled by configuring tip 72 accordingly, as will be recognized by the skilled artisan.

Figure 11:
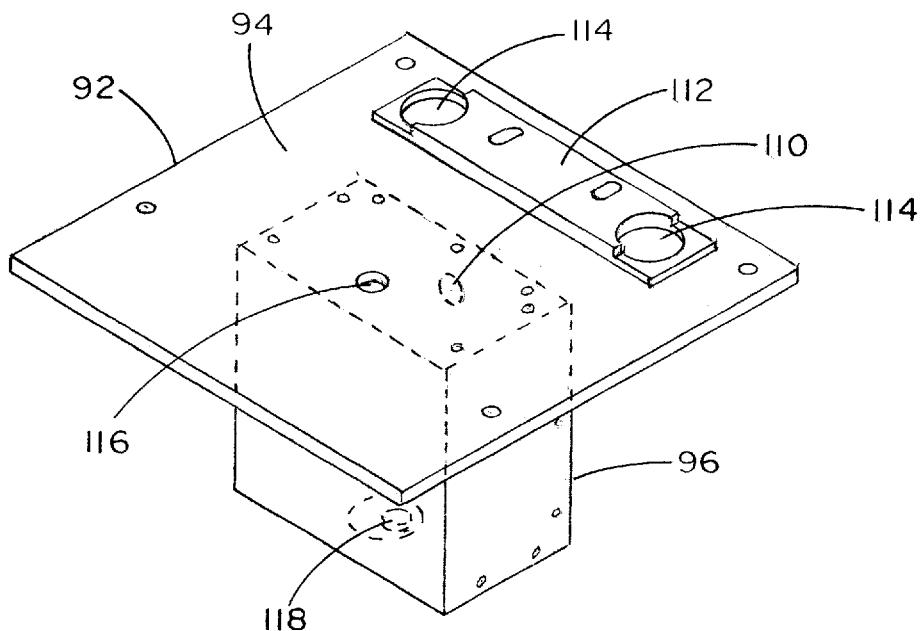
FIG. 11 is a top perspective view of the optional weighing isolation housing of the apparatus.
Figure 12:
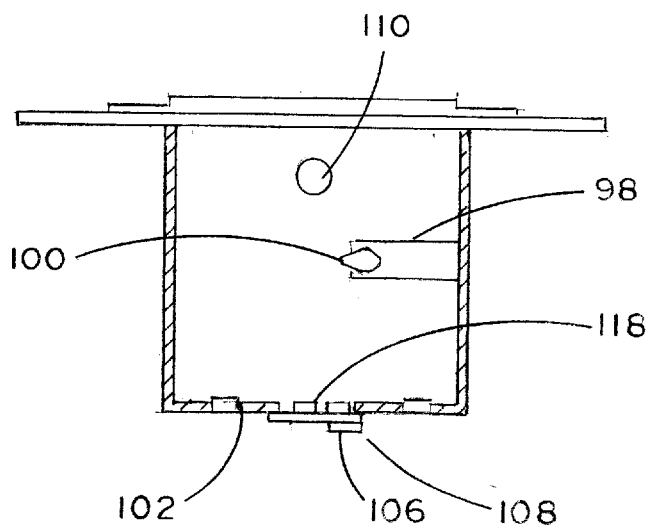
FIG. 12 is a side elevational view of the optional weighing isolation housing.

The forward portion of sample handling assembly 8 may be isolated to facilitate certain weighing operations which require greater isolation of the sample or control of the atmospheric environment during the operation. Housing 92 may be optionally installed to provide this capacity (see FIG. 13). FIGS. 11 and 12 provide a top perspective and front elevational view, respectively, showing details of housing 92 (apparatus not shown). Top mounting plate 94 is provided with connection apertures 114 and bracket 112 for connecting housing 92 to the bottom of balance 6. Aperture 116 allows passage of balance shaft 40 of the gripper assembly 24 to balance 6 when housing 92 is installed (gripper assembly 24 is contained within housing 92).

The lower compartment 96 of housing 92 is a substantially rectangular box having front and rear, left and right, and bottom plate 102 (see FIG. 12), with the top formed by attachment lower compartment 96 to top mounting plate 94. Aperture 110, in the rear side of lower compartment 96, allows passage of outer and inner shafts 58 and 57, such that gripper assembly 24 may be actuated within housing 92. FIG. 12 shows lifted sample sensor 100, secured by sensor bracket 98. Seated sample sensor 106 is secured by sensor bracket 108. Seated sample sensor 106 and bracket 108 are positioned adjacent to aperture 118, which allows lifting of a sample container 30 (see FIGS. 5 and 6) through bottom plate 102 by lifting assembly 14. Together this sensor arrangement allows precise coordination of the operation of lift assembly 14 and sample handling assembly 8, when housing 96 is utilized.

Figure 13:
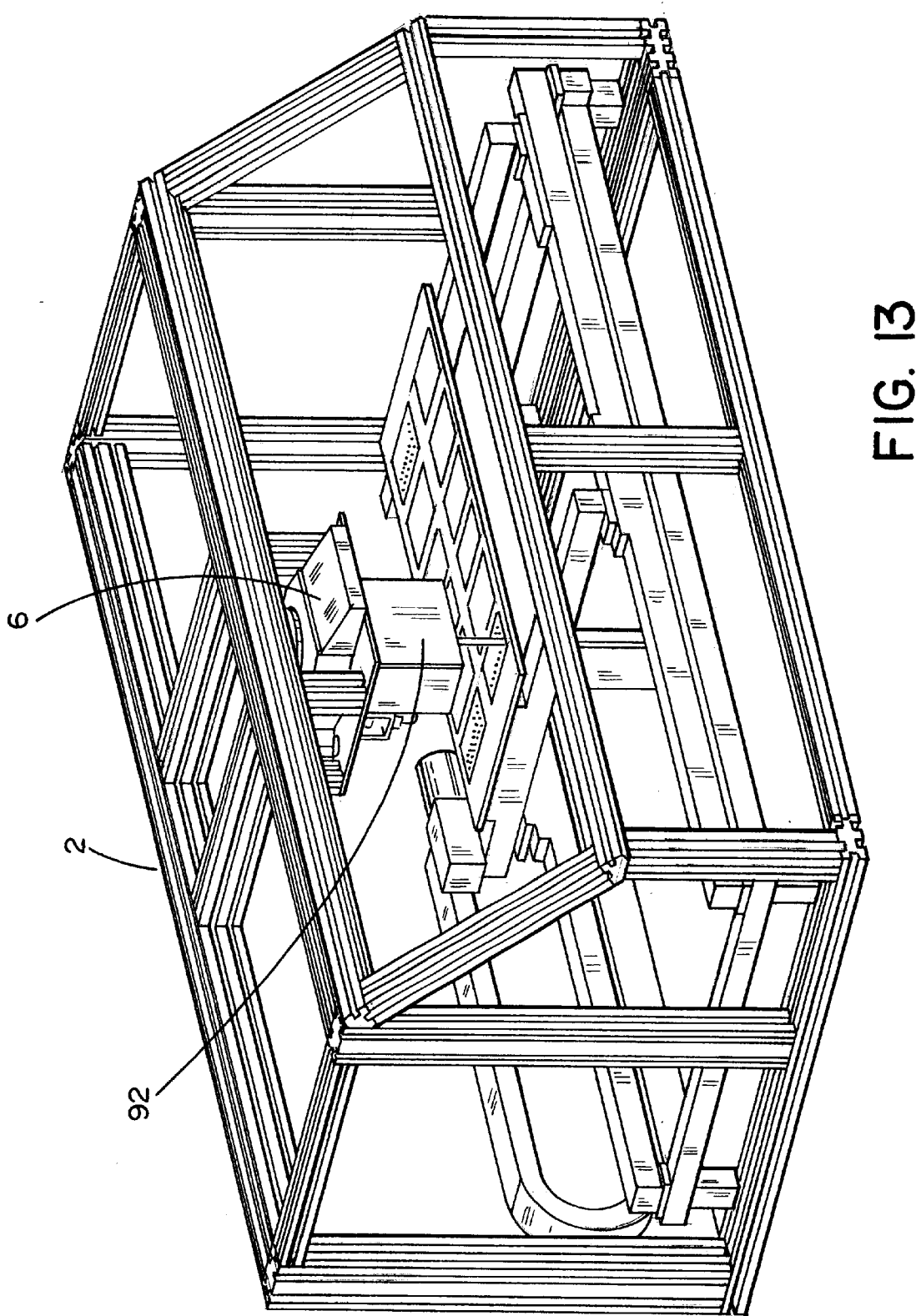
FIG. 13 is a front perspective view of one embodiment of the apparatus having the optional weighing isolation housing installed.

FIG. 13 shows an embodiment of automated weighing station 2, with housing 92 installed.

It will thus be seen that the objects set forth, among those made apparent from the preceding description, are efficiently obtained and, since certain changes may be made in carrying out the above embodiments and in the apparatus and method set forth, without departing from the spirit and scope of the invention, it is intended that all matter contained in the above description shall be interpreted as illustrative and not in a limiting sense.

It is also to be understood that the following claims are intended to cover all of the generic and specific features of the invention herein described and all statements of the scope of the invention which, as a matter of language, might be said to fall there between.

Figure 14:
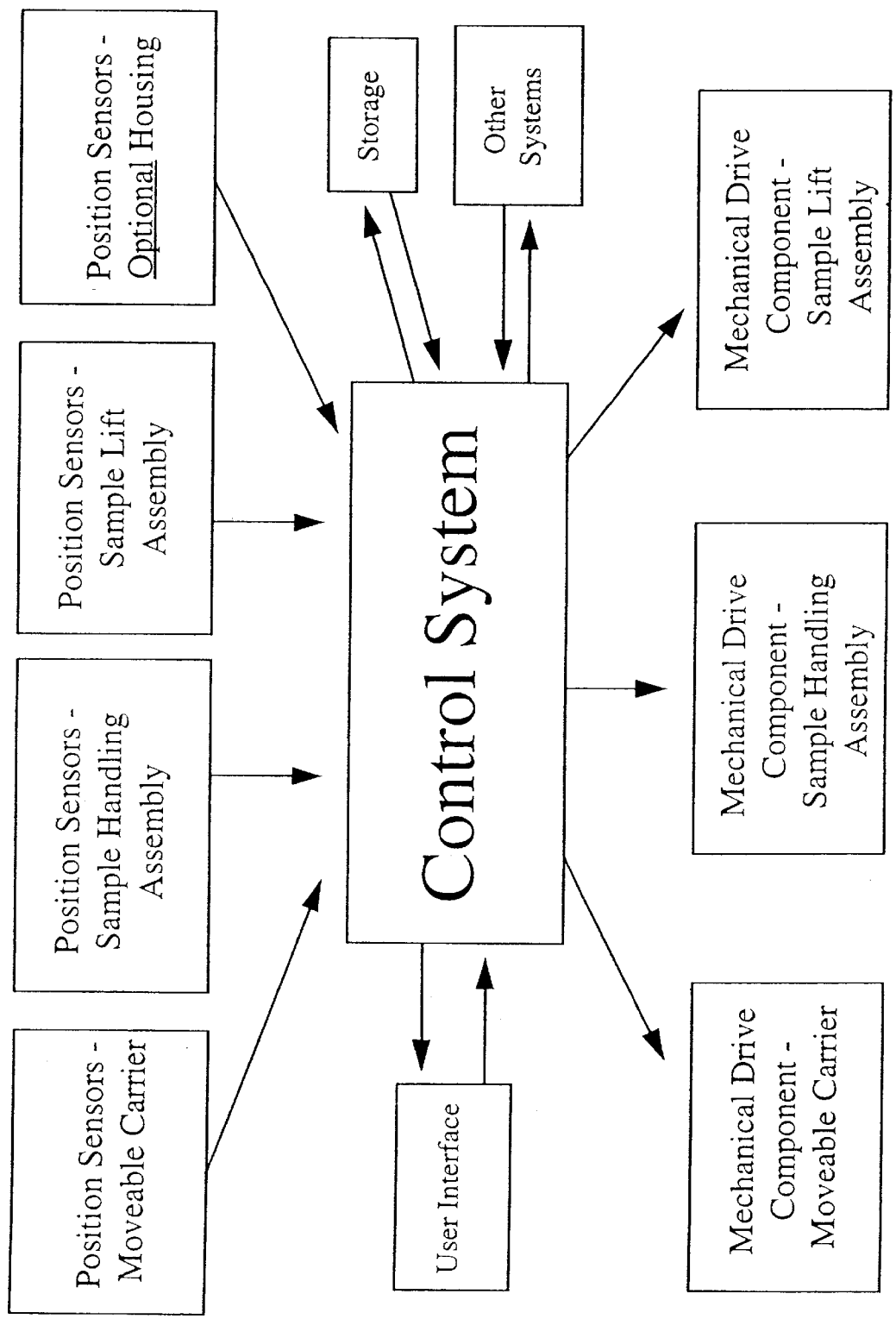
FIG. 14 is a block diagram of the control system, associated devices, and systems, according to one embodiment of the invention.

FIG. 14 is a block diagram of the control system, associated devices, and systems, according to one embodiment of the invention, wherein the blocks represent modules in the system and the arrows depict data flow to/from the modules.

What is claimed is:

1. An automated weighing station comprising,
    a) a support frame;
    b) a balance secured to said support frame;
    c) a sample handling assembly operably connected to said balance and secured to said balance;
    d) a moveable carrier capable of moving samples in at least a plurality of directions for moving samples into position beneath said sample handling assembly;
    e) a lift assembly positioned beneath said moveable carrier and said sample handling assembly for lifting samples into position to be accessed by said sample handling assembly; and
    f) a control system for controlling said sample handling assembly, said lift assembly, and said moveable carrier in a coordinated manner, and for storing weight measurements of individual samples.

2. An automated weighing station of claim 1, wherein said sample handling assembly further comprises,
    a) a gripper assembly comprising arms, one end of each arm being pivotably connected along a common pivot axis, and the opposite end of each arm comprising a gripper finger adapted to directly contact a sample container, and a spring tensioner urging said arms toward one another; and
    b) a powered mechanical drive component in communication with said gripper assembly.

3. An automated weighing station of claim 2, wherein said mechanical drive component operates intermittently to spread said gripper arms against the force of said spring tensioner, thereby increasing the distance between said gripper fingers of the respective gripper arms such that a sample may be received therein, to be gripped by said fingers when said mechanical drive component releases said arms to return to a closed position as urged by said spring tensioner.

4. An automated weighing station of claim 1, wherein said moveable carrier comprises,
    a) a sample rack carrier; and
    b) a carrier support unit.

5. An automated weighing station of claim 4, further comprising position sensors adapted to communicate the position of said sample rack carrier in relation to said gripper assembly, to said control system such that weight measurements of individual samples are stored electronically, and are associated with an individual sample by at least one identifying characteristic.

6. An automated weighing station of claim 4, wherein said sample racks are characterized by an asymmetric shape which requires that said sample racks be placed in said sample rack carrier in only one possible orientation relative to said moveable carrier.

7. An automated weighing station of claim 4, further comprising a scanner for determining the identity of sample racks within an array of racks held by said sample rack carrier.

8. An automated weighing station of claim 7, wherein said sample rack carrier comprises openings such that said scanner may determine the identity of sample racks disposed within the interior of said array of racks.

9. An automated weighing station of claim 7, wherein said sample racks are identified by said scanner utilizing a bar coding system.

10. An automated weighing station of claim 4, wherein said sample rack carrier is adapted to hold at least one rack which is adapted to hold a plurality of sample containers.

11. An automated weighing station of claim 4, wherein said sample rack carrier is adapted to allow access by said lift assembly to at least one sample container from beneath said sample rack carrier.

12. An automated weighing station of claim 4, wherein said carrier support unit further comprises at least one powered mechanical drive component adapted to provide controlled forward and rearward, left and right movement of said sample rack carrier.

13. An automated weighing station of claim 12, where said at least one powered mechanical drive component comprises a first electric motor controlling forward and rearward movement, and a second electric motor controlling left and right movement of said sample rack carrier.

14. An automated weighing station of claim 1, wherein said lift assembly comprises,
    a) a housing;
    b) a powered mechanical drive component connected to said housing; and
    c) a lift shaft operably connected to said powered mechanical drive component, wherein said powered mechanical drive component provides controlled upward and downward movement of said lift shaft.

15. An automated weighing station of claim 14, wherein said lift shaft further comprises a tip which is adapted to receive the bottom portion of a sample container.

16. An automated weighing station of claim 15, wherein said tip is adapted to receive a bottom portion of a sample container, the shape of which is selected from the group consisting of rounded, conical, flat-ended cubical, and flat-ended circular.

17. An automated weighing station of claim 14, wherein said powered mechanical drive component comprises an electric motor having a pulley engaged to a belt member, the distal portion of which engages a second pulley, and wherein said belt member is attached to a lift shaft mount to provide upward and downward motion of said lift shaft which is connected to said lift shaft mount.

18. An automated weighing station of claim 1, further comprising a housing adapted to isolate a gripper assembly of said sample handling assembly.

19. An automated weighing station of claim 18, wherein said housing comprises a first sensor associated with an aperture for receiving a sample through a bottom plate of said housing, and a second sensor positioned adjacent to said gripper assembly, said first and second sensors allowing determination of a lowered position and a lifted position, respectively, of said sample.

20. An automated weighing station of claim 17, wherein said housing further comprises at least one aperture for the introduction of gases for atmospheric control within said housing.

21. A method of weighing multiple individual samples, said method comprising moving an ordered array of sample containers in at least a plurality of orthogonal directions beneath a stationary sample handling assembly, elevating at least one sample container, reversibly securing said at least one sample container to a gripper assembly of said stationary sample handling assembly, weighing the sample container, storing the weight and position of the sample container, and returning said at least one sample container to said ordered array after a weight measurement is taken, wherein said gripper assembly is connected to a balance and is disengaged from other components of said sample handling assembly while said weight measurement is taken.

22. A method of claim 21, wherein the weight of a sample within the individual sample container is between about 0.01 mg and about 500 g.

23. A method of claim 21, wherein the weight of a sample within the individual sample container is between about 0.1 mg and about 50 g.

24. A method of claim 21, wherein the weight of a sample within the individual sample container is between about 1 mg and about 5 g.

25. A method of claim 21, wherein the weight of a sample within said individual sample container is between about 1 mg and about 100 mg.

26. A method of claim 21, wherein the weight of a sample within said individual sample container is between about 2 mg and about 50 mg.

27. A method of claim 21, wherein the weight of a sample within said individual sample container is between about 5 mg and about 25 mg.

28. A weighing system for automated weighing of samples, said system comprising,
   a support frame;
   a balance secured to said support frame;
   a sample handling assembly operatively connected to said balance and secured to said balance;
   a moveable carrier capable of moving samples in at least a plurality of directions for moving samples into position beneath said sample handling assembly;
   a lift assembly positioned beneath said moveable carrier and said sample handling assembly for lifting samples into position to be accessed by said sample handling assembly; and
   a data handling system for storing and processing of weight measurements of said samples.

29. A weighing system of claim 28, wherein said data handling system comprises a balance; computer software; and computer hardware; wherein said data handling system is adapted to communicate weight measurements to computer software and hardware.

30. A weighting system of claim 29, wherein said data handling system further comprises one or more data collectors positioned and adapted to transmit information to a computer control unit, thereby allowing coordinated movement of samples via said sample handing assembly, said moveable carrier, and said lift assembly, wherein said information is coordinated by said computer control unit with the storage of weight measurement transmitted by said balance for individual samples.

31. A weighing system of claim 29, wherein said data handling system further comprises a scanner for detection of the position and identity of sample racks on said moveable carrier; at least one position sensor associated with said moveable carrier; and at least one sample position sensor associated with said sample handling assembly.

32. A weighing system of claim 29, wherein said computer hardware comprises one or more of the following: a display; data entry apparatus; a processor; an interface to the weighing apparatus; a printer or other output apparatus; electronic interfaces among the component parts; and memory.

33. A weighing system of claim 29, wherein said computer software comprises an operating system; a database program; a report generating program; a data-receiving program for receiving data from the weighing apparatus; and a control program for controlling the weighing apparatus.

34. A weighing system of claim 33, wherein said report generating program is adapted to provide data comprising individual sample identification related one or more of sample rack identity, sample position, tare weight of a sample container, gross weight of sample and sample container, and net weight of said sample.

35. A weighing system of claim 34, wherein said data is originally stored in a format selected from the group consisting of ASCII text, binary, and ODBC (object database connectivity format).

36. A weighing system of claim 34, wherein said data is originally stored in ASCII text format.

37. An automated weighing station comprising:
   a) a support frame;
   b) a balance secured to said support frame;
   c) a sample handling assembly operably connected to said balance and secured to said balance;
   d) a moveable carrier for moving samples into position beneath said sample handling assembly;
   e) a lift assembly positioned beneath said moveable carrier and said sample handling assembly for lifting samples into position to be accessed by said sample handling assembly; and
   f) a control system for controlling said sample handling assembly, said lift assembly, and said moveable carrier in a coordinated manner, and for storing weight measurements of individual samples,
   wherein said sample handling assembly further comprises,
      a gripper assembly comprising arms, one end of each arm being pivotably connected along a common pivot axis, and the opposite end of each arm comprising a gripper finger adapted to directly contact a sample container,
      and a spring tensioner urging said arms toward one another; and
   a powered mechanical drive component in communication with said gripper assembly.

38. An automated weighing station of claim 37, wherein said mechanical drive component operates intermittently to spread said gripper arms against the force of said spring tensioner, thereby increasing the distance between said gripper fingers of the respective gripper arms such that a sample may be received therein, to be gripped by said fingers when said mechanical drive component releases said arms to return to a closed position as urged by said spring tensioner.

39. An automated weighing station comprising:
   a) a support frame;
   b) a balance secured to said support frame;
   c) a sample handling assembly operably connected to said balance and secured to said balance;
   d) a moveable carrier for moving samples into position beneath said sample handling assembly;
   e) a lift assembly positioned beneath said moveable carrier and said sample handling assembly for lifting samples into position to be accessed by said sample handling assembly; and
   f) a control system for controlling said sample handling assembly, said lift assembly, and said moveable carrier in a coordinated manner, and for storing weight measurements of individual samples, wherein said moveable carrier comprises,
i) a sample rack carrier; and
ii) a carrier support unit.

40. An automated weighing station of claim 39, further comprising position sensors adapted to communicate the position of said sample rack carrier in relation to said gripper assembly, to said control system such that weight measurements of individual samples are stored electronically, and are associated with an individual sample by at least one identifying characteristic.

41. An automated weighing station of claim 39, wherein said sample racks are characterized by an asymmetric shape which requires that said sample racks be placed in said sample rack carrier in only one possible orientation relative to said moveable carrier.

42. An automated weighing station of claim 39, further comprising a scanner for determining the identity of sample racks within an array of racks held by said sample rack carrier.

43. An automated weighing station of claim 42, wherein said sample rack carrier comprises openings such that said scanner may determine the identity of sample racks disposed within the interior of said array of racks.

44. An automated weighing station of claim 42, wherein said sample racks are identified by said scanner utilizing a bar coding system.

45. An automated weighing station of claim 39, wherein said sample rack carrier is adapted to hold at least one rack which is adapted to hold a plurality of sample containers.

46. An automated weighing station of claim 39, wherein said sample rack carrier is adapted to allow access by said lift assemble to at least one sample container from beneath said sample rack carrier.

47. An automated weighing station of claim 39, wherein said carrier support unit further comprises at least one powered mechanical drive component adapted to provide controlled forward and rearward, left and right movement of said sample rack carrier.

48. An automated weighing station of claim 47, where said at least one powered mechanical drive component comprises a first electric motor controlling forward and rearward movement, and a second electric motor controlling left and right movement of said sample rack carrier.

49. An automated weighing station of claim 37, wherein said lift assembly comprises,
a) a housing;
b) a powered mechanical drive component connected to said housing; and
c) a lift shaft operably connected to said powered mechanical drive component, wherein said powered mechanical drive component provides controlled upward and downward movement of said lift shaft.

50. An automated weighing station of claim 49, wherein said lift shaft further comprises a tip which is adapted to receive the bottom portion of a sample container.

51. An automated weighing station of claim 50, wherein said tip is adapted to receive a bottom portion of a sample container, the shape of which is selected from the group consisting of rounded, conical, flat-ended cubical, and flatended circular.

52. An automated weighing station comprising:
a) a support frame;
b) a balance secured to said support frame;
c) a sample handling assembly operably connected to said balance and secured to said balance;
d) a moveable carrier for moving samples into position beneath said sample handling assembly;
e) a lift assembly positioned beneath said moveable carrier and said sample handling assembly for lifting samples into position to be accessed by said sample handling assembly; and
f) a control system for controlling said sample handling assembly, said lift assembly, and said moveable carrier in a coordinated manner, and for storing weight measurements of individual samples, wherein said lift assembly comprises,
i) a housing;
ii) a powered mechanical drive component connected to said housing; and
iii) a lift shaft operably connected to said powered mechanical drive component, wherein said powered mechanical drive component provides controlled upward and downward movement of said lift shaft, wherein said powered mechanical drive component comprises an electric motor having a pulley engaged to a belt member, the distal portion of which engages a second pulley, and wherein said belt member is attached to a lift shaft mount to provide upward and downward motion of said lift shaft which is connected to said lift shaft mount.

53. An automated weighing station comprising:
a) a support frame;
b) a balance secured to said support frame;
c) a sample handling assembly operably connected to said balance and secured to said balance;
d) a moveable carrier for moving samples into position beneath said sample handling assembly;
e) a lift assembly positioned beneath said moveable carrier and said sample handling assembly for lifting samples into position to be accessed by said sample handling assembly; and
f) a control system for controlling said sample handling assembly, said lift assembly, and said moveable carrier in a coordinated manner, and for storing weight measurements of individual samples, wherein the automated weighing station further comprises a housing adapted to isolate a gripper assembly of said sample handling assembly.

54. An automated weighing station of claim 53, wherein said housing comprises a first sensor associated with an aperture for receiving a sample through a bottom plate of said housing, and a second sensor positioned adjacent to said gripper assembly, said first and second sensors allowing determination of a lowered position and a lifted position, respectively, of said sample.

55. An automated weighing station of claim 52, wherein said housing further comprises at least one aperture for the introduction of gases for atmospheric control within said housing.

56. A weighing system comprising:
a support frame;
a balance secured to said support frame;
a sample handling assembly operatively connected to said balance and secured to said balance;
a moveable carrier for moving samples into position beneath said sample handling assembly;
a lift assembly positioned beneath said moveable carrier and said sample handling assembly for lifting samples into position to be accessed by said sample handling assembly; and a data handling system for storing and processing of weight measurements of said samples, wherein said data handling system comprises a balance; computer software; and computer hardware; wherein said data handling system is adapted to communicate weight measurements to computer software and hardware.

57. A weighting system of claim 56, wherein said data handling system further comprises one or more data collectors positioned and adapted to transmit information to a computer control unit, thereby allowing coordinated movement of samples via said sample handing assembly, said moveable carrier, and said lift assembly, wherein said information is coordinated by said computer control unit with the storage of weight measurement transmitted by said balance for individual samples.

58. A weighing system of claim 56 wherein said data handling system further comprises a scanner for detection of the position and identity of sample racks on said moveable carrier; at least one position sensor associated with said moveable carrier; and at least one sample position sensor associated with said sample handling assembly.

59. A weighing system of claim 56, wherein said computer hardware comprises one or more of the following: a display; data entry apparatus; a processor; an interface to the weighing apparatus; a printer or other output apparatus; electronic interfaces among the component parts; and memory.

60. A weighing system of claim 56, wherein said computer software comprises an operating system; a database program; a report generating program; a data-receiving program for receiving data from the weighing apparatus; and a control program for controlling the weighing apparatus.

61. A weighing system of claim 60, wherein said report generating program is adapted to provide data comprising individual sample identification related one or more of sample rack identity, sample position, tare weight of a sample container, gross weight of sample and sample container, and net weight of said sample.

62. A weighing system of claim 61, wherein said data is originally stored in a format selected from the group consisting of ASCII text, binary, and ODBC (object database connectivity format).

63. A weighing system of claim 61, wherein said data is originally stored in ASCII text format.

64. A method of weighing multiple individual samples, said method comprising moving an ordered array of sample containers in at least a plurality of orthogonal directions beneath a stationary sample handling assembly, elevating at least one sample container, reversibly securing said at least one sample container to a gripper assembly of said stationary sample handling assembly, and returning said at least one sample container to said ordered array after a weight measurement is taken, wherein said gripper assembly is connected to a balance and is disengaged from other components of said sample handling assembly while said weight measurement is taken, wherein the weight of a sample within the individual sample container is between about 0.01 mg and about 500 g.

65. A method of weighing multiple individual samples, said method comprising moving an ordered array of sample containers in at least a plurality of orthogonal directions beneath a stationary sample handling assembly, elevating at least one sample container, reversibly securing said at least one sample container to a gripper assembly of said stationary sample handling assembly, and returning said at least one sample container to said ordered array after a weight measurement is taken, wherein said gripper assembly is connected to a balance and is disengaged from other components of said sample handling assembly while said weight measurement is taken, wherein the weight of a sample within the individual sample container is between about 0.1 mg and about 50 g.

66. A method of weighing multiple individual samples, said method comprising moving an ordered array of sample containers in at least a plurality of orthogonal directions beneath a stationary sample handling assembly, elevating at least one sample container, reversibly securing said at least one sample container to a gripper assembly of said stationary sample handling assembly, and returning said at least one sample container to said ordered array after a weight measurement is taken, wherein said gripper assembly is connected to a balance and is disengaged from other components of said sample handling assembly while said weight measurement is taken, wherein the weight of a sample within the individual sample container is between about 1 mg and about 5 g.

67. A method of weighing multiple individual samples, said method comprising moving an ordered array of sample containers in at least a plurality of orthogonal directions beneath a stationary sample handling assembly, elevating at least one sample container, reversibly securing said at least one sample container to a gripper assembly of said stationary sample handling assembly, and returning said at least one sample container to said ordered array after a weight measurement is taken, wherein said gripper assembly is connected to a balance and is disengaged from other components of said sample handling assembly while said weight measurement is taken, wherein the weight of a sample within said individual sample container is between about 1 mg and about 100 mg.

68. A method of weighing multiple individual samples, said method comprising moving an ordered array of sample containers in at least a plurality of orthogonal directions beneath a stationary sample handling assembly, elevating at least one sample container, reversibly securing said at least one sample container to a gripper assembly of said stationary sample handling assembly, and returning said at least one sample container to said ordered array after a weight measurement is taken, wherein said gripper assembly is connected to a balance and is disengaged from other components of said sample handling assembly while said weight measurement is taken, wherein the weight of a sample within said individual sample container is between about 2 mg and about 50 mg.

69. A method of weighing multiple individual samples, said method comprising moving an ordered array of sample containers in at least a plurality of orthogonal directions beneath a stationary sample handling assembly, elevating at least one sample container, reversibly securing said at least one sample container to a gripper assembly of said stationary sample handling assembly, and returning said at least one sample container to said ordered array after a weight measurement is taken, wherein said gripper assembly is connected to a balance and is disengaged from other components of said sample handling assembly while said weight measurement is taken, wherein the weight of a sample within said individual sample container is between about 5 mg and about 25 mg.

* * * * *

UNITED STATES PATENT AND TRADEMARK OFFICE
CERTIFICATE OF CORRECTION

| | |
|---|---|
| PATENT NO. | : 6,539,334 B1 |
| APPLICATION NO. | : 09/611393 |
| DATED | : March 25, 2003 |
| INVENTOR(S) | : Reyad I. Sawafta |

It is certified that error appears in the above-identified patent and that said Letters Patent is hereby corrected as shown below:

On the title page under (*) Notice – the phrase "U.S.C. 154(b) by 120 days" should read -- U.S.C. 154(b) by 233 days --

In Column 1, Line 42 – the word "on e" should read -- one --

In Column 2, Line 2 – the word "objection" should read -- object --

In Column 2, Line 31 – the word "provide" should read -- provides --

In Column 6, Line 40 – the words "related one" should read -- related to one --

In Column 7, Line 60 – the word "via." should read -- via --

In Column 7, Line 64 – the word "operators" should read -- operates --

In Column 8, Line 48 – the words "attachment lower" should read -- attachment of lower --

In Column 9, Line 19 – the phrase that reads "a plurality of directions" should read -- a plurality of orthogonal directions --

In Column 11, Line 34 – the phrase that reads "a plurality of directions" should read -- a plurality of orthogonal directions --

In Column 11, Line 47 – the word "weighting" should read -- weighing --

In Column 12, Line 8 – the words "related one" should read -- related to one --

In Column 12, Line 24 – the phrase that reads "moveable carrier for moving samples into position" should read -- moveable carrier capable of moving samples in at least a plurality of orthogonal directions for moving samples into position --

In Column 12, Line 60 – the phrase that reads "moveable carrier for moving samples into position" should read -- moveable carrier capable of moving samples in at least a plurality of orthogonal directions for moving samples into position --

In Column 13, Line 34 – the word "assemble" should read -- assembly --

UNITED STATES PATENT AND TRADEMARK OFFICE
CERTIFICATE OF CORRECTION

| | |
|---|---|
| PATENT NO. | : 6,539,334 B1 |
| APPLICATION NO. | : 09/611393 |
| DATED | : March 25, 2003 |
| INVENTOR(S) | : Reyad I. Sawafta |

It is certified that error appears in the above-identified patent and that said Letters Patent is hereby corrected as shown below:

In Column 14, Line 1 – the phrase that reads "moveable carrier for moving samples into position" should read -- moveable carrier capable of moving samples in at least a plurality of orthogonal directions for moving samples into position --

In Column 14, Line 32 – the phrase that reads "moveable carrier for moving samples into position" should read -- moveable carrier capable of moving samples in at least a plurality of orthogonal directions for moving samples into position --

In Column 14, Line 62 – the phrase that reads "moveable carrier for moving samples into position" should read -- moveable carrier capable of moving samples in at least a plurality of orthogonal directions for moving samples into position --

In Column 15, Line 8 – the word "weighting" should read -- weighing --

In Column 15, Line 35 – the words "related one" should read -- related to one --

Signed and Sealed this

Twenty-sixth Day of June, 2007

JON W. DUDAS
*Director of the United States Patent and Trademark Office*